United States Patent [19]

Hao

[11] Patent Number: 4,780,529

[45] Date of Patent: Oct. 25, 1988

[54] ISOLATION OF AN ENDOTOXIN INACTIVATOR FROM HUMAN PLASMA, AND METHODS OF USE

[75] Inventor: Yu-Lee Hao, Potomac, Md.

[73] Assignee: Biotech Research Laboratories, Inc., Rockville, Md.

[21] Appl. No.: 62,700

[22] Filed: Jun. 16, 1987

Related U.S. Application Data

[62] Division of Ser. No. 764,253, Aug. 9, 1985, Pat. No. 4,677,194.

[51] Int. Cl.$^4$ .................. A61L 2/00; A61K 35/14; A61K 37/02; A61K 39/395
[52] U.S. Cl. ........................... 530/350; 530/351; 530/363; 530/364; 530/380; 530/387; 530/388; 530/412; 530/829
[58] Field of Search ............... 530/350, 351, 363, 364, 530/380, 387, 388, 412, 829

[56] References Cited

U.S. PATENT DOCUMENTS

| | | | |
|---|---|---|---|
| 4,069,216 | 1/1978 | Shanbrom | 530/387 |
| 4,382,028 | 5/1983 | Paget | 424/101 |
| 4,639,513 | 1/1987 | Hou et al. | 530/414 |
| 4,719,290 | 1/1988 | Curry et al. | 530/387 |

FOREIGN PATENT DOCUMENTS 2065129A  6/1981  United Kingdom ................ 530/414

OTHER PUBLICATIONS

Skarnes et al., *J. Exp. Med.*, vol. 108, (1958), pp. 685–700.
Landy et al., *J. Exp. Med.*, vol. 110 (1959), pp. 731–750.
Johnson et al., *Amer. Jour. of Path.*, vol. 88, No. 3, (1977), pp. 559–574.
Tewlesbury et al., "Purification of Human Angiotensinogen", Supp. II, *Circ. Res.*, vol. 41, No. 41, Oct. 1977, pp. II29–II33.
CA vol. 72, 1970, 88461w Inoue et al.

*Primary Examiner*—John Kight
*Assistant Examiner*—Nathan M. Nutter
*Attorney, Agent, or Firm*—Iver P. Cooper

[57] ABSTRACT

An endotoxin inactivator is isolated from human plasma by anion exchange (DEAE-Sephadex), dye-affinity (Cibracron Blue-Sepharose), and adsorption (on hydroxyapatite) chromatography. The endotoxin inactivator, isolated in essentially pure form, may be used to depyrogenate clinical blood products.

11 Claims, 3 Drawing Sheets

A B

A B

ISOLATION OF AN ENDOTOXIN INACTIVATOR FROM HUMAN PLASMA, AND METHODS OF USE

This application is a division of Ser. No. 764,253, filed Aug. 9, 1985, issued June 30, 1987 as U.S. Pat. No. 4,667,194, and priority is claimed therefrom pursuant to 35 U.S.C. 120.

BACKGROUND OF THE INVENTION

The present invention relates the isolation from human plasma of an endotoxin-inactivator which could be added to pyrogenic lots of blood products, such as albumin, immune globulins, antihemophilic factor (AHF) concentrates, Factor IX concentrates, interferons, fibronectin and others, thus rendering them non-pyrogenic, and again suitable for clinical use.

Pyrogenicity in blood products is caused by contamination from endotoxins of Gram-negative bacteria during the manufacturing process. Because of the ubiquitous nature of bacteria, the control of these physiologically active agents is of utmost importance to the plasma fractionation industry, as well as to the entire pharmaceutical industry. The most positive method of control, strict aseptic techniques that limit microbial contamination, cannot, in most cases, maintain complete sterility throughout the manufacturing process. Therefore, manufacturers may at times find their final products pyrogenic at the bulk solution stage prior to filling. The result may be loss of the entire lot, or only partial recovery.

In the plasma fractionation industry the monetary loss due to pyrogenic products may be measured in millions of dollars per year. However, no plasma fractionator has used or reported any means to depyrogenate their endotoxin-contaminated products except that, in the case of depyrogenation of albumin, there are two documented methods.

The first published method for depyrogenation of clinical albumin was reported by Wye and Kim (Vox Sang 32: 182–184, 1977) who mixed pyrogenic albumin with Cohn ethanol fractions IV-1 and IV-4, based on the findings of Yoshioka and Johnson (J. Immunol. 89: 326–335, 1962), followed by differential thermal heating to recover albumin according to the method of Schneider et al. (Blut 30: 121–134, 1975). The reported method not only requires an excessive amount of Cohn Fractions IV-1 and IV-4, but also suffers considerable losses of albumin. The yield based on 21 batches was about 75%. In some cases, the procedure has to be repeated thus resulting in further losses.

The second method for depyrogenation of albumin was developed by this inventor. It is described in his SN 06/635,134, filed July 27, 1984 and now abandoned. This method is based on the finding that plasma contains "enzyme(s)" which could detoxify the endotoxins. Pyrogenic albumin was mixed with sufficient plasma to detoxify all endotoxins present. The albumin was then purified to over 99%. (Hao, Vox Sang 36: 313–320, 1979). The resultant albumin had a non-detectable level of endotoxin (less than 0.05 ng/ml) as assayed by Limulus Amebocyte Lysate (LAL) test (Levin et al. J. Lab. Clin. Med. 75: 903, 1970) and confirmed by the USP rabbit pyrogen test.

Obviously, the addition of plasma cannot be used for depyrogenation of other clinical plasma products, such as antihemophilic factor (AHF), immune serum globulin (ISG), Factor IX complex concentrate and plasma protein fraction (PPF), since the resulting product would then contain undesired plasma proteins.

It has been known for over 30 years since the first report by Hegemann (Z. Immunitactsforsch 111: 213–225, 1954) that normal human plasma (serum) has the ability to diminish the pyrogenicity of endotoxin derived from the Gram-negative bacteria. This observation was confirmed in subsequent years by many reports (Skarnes et al., J. Exp. Med. 108: 685–700, 1958; Rall et al., Am. J. Physiol. 188: 559–562, 1957; Rudbach and Johnson, Nature 202: 811–812, 1964; Yoshioka and Johnson, J. Immunol. 89: 326–335, 1962; Landy et al. J. Exp. Med. 110: 731–750, 1959; Skarnes, Ann. N.Y. Acad. Sci. 133: 644–662, 1966). Landy et al. (1959) and Skarnes (1966) further suggested that the detoxifying effect by serum (or plasma) is of an enzymatic nature. Yoshioka and Johnson (1962) fractionated serum by the Cohn ethanol procedure (Cohn et al. JACS 68: 459–475, 1946) and found that Cohn Fraction IV-1 contains the substance(s) which decrease pyrogenicity caused by endotoxins. Skarnes (1966), using plasma fractions obtained from ion exchange chromatography, found that the esterase associated with the alpha-1-lipoprotein appeared responsible for degradation of endotoxin, and an alpha-1-globulin esterase appeared responsible for inactivation of endotoxin.

According to Skarnes, "numerous attempts were made to purify the $IV_c$ fraction in order to separate the active enzymes. However, neither cellulose nor sephadex columns were well suited to the purpose and although subfractions were obtained which were rich in either the lipoprotein esterase or the a1-globulin esterase, all such fractions contained both esterases."

Johnson et al. (Amer. J. pathol. 88: 559–574, 1977) later isolated from human serum a single inactivator which was neither a lipoprotein, nor a serine esterase. They did, however, find esterase activity associated with a partially purified inactivator in a sucrose density gradient system, even though, for unknown reasons, they did not proceed to isolate this protein in pure form.

Johnson's inactivator "LPS-1" was isolated by a six-step procedure: fractional precipitation of plasma with ammonium sulfate at 40–60% saturation; gel filtration on Sephadex G-150; anion exchange chromatography on DEAE-cellulose; gel filtration on Sephadex G-200; hydroxylapatite chromatography; and preparative gel electrophoresis. I found that this procedure was too long and too tedious. Even though extreme caution was taken to ensure that every piece of glassware, chemicals, reagents, and every piece of equipment was pyrogen-free, it was very difficult to maintain them pyrogen-free since each step required lengthly dialysis and concentration of the sample. Therefore, many a time a partially purified fraction was found to have lost its activity at some stage during purification. There was no way of knowing whether the loss of activity was due to contamination of endotoxins or denaturation of the inactivator itself. During purification, it became obvious that the original procedure called for so many steps mainly for the removal of a major contaminant, albumin. I found that bulk of the albumin could be removed at the DEAE-Sephadex step if stepwise elution at 0.15M NaCl concentration was used. By the use of Cibacron-Blue Sepharose (CBS) right after DEAE-Sephadex step, I removed the remaining albumin. I used the same buffer system (0.02M phosphate buffer, pH 7.35) in both steps so that the DEAE-eluate could be simply diluted 3-fold or diafiltered prior to application to CBS column. Because of the complete removal of albumin, a highly purified EI could be readily obtained by hydroxylapatite chromatography thus eliminating the steps of gel filtration on G-150 and G-200 and preparative gel electrophoresis (taught by Johnson) which would have been a bottleneck if large quantities of EI were to be prepared.

Endotoxins are high molecular weight complexes, associated with the outer membrane of Gram-negative bacteria that induce pyrogenic reactions upon intravenous administration. Endotoxins contain lipid, carbohydrate and protein. Purfied endotoxins do not contain protein, and therefore, are referred to as lipopolysaccharide (LPS). It has been shown that LPS contains three distinct chemical regions; Region I, O-specific polysaccharide carrying the main serologic specificity, is linked to the core polysaccharide, known as Region II. This core material is linked in turn to the lipid component--Region III or Lipid A. (Westphal, O. Int. Archs. Allergy Appl. Immun. 49: 1–43; 1975 and Bradley, S.G. Ann. Rev. Microbial. 33: 67–94, 1979).

It is the lipid A which is responsible for most, if not all, of the biological activities of endotoxin (Galanos, et al. Eur. J. Biochem. 19: 145–152, 1971; Galanos, et al. Eur. J. Biochem. 22: 218–224, 1971; Luderitz, et al. The Chemistry Biology and Clinical Significance of Endotoxins Univ. of Chicago Press, pp. 9–21, 1973; Rietschel et al. Infect. Immunity 8: 173–177, 1973). For example, when free lipid A is complexed with bovine serum albumin, or human serum albumin, pyrogenicity is induced comparable to that of intact endotoxin according to rabbit pyrogen test (Galanos et al. 1972; and Rietschel et al. 1973). Furthermore, the activity of Lipid A derived from E. coli and various strains of Salmonella are similar and the pattern of febril response is identical to that produced by intact endotoxin (Luderitz et al. 1973).

Lipid A is composed of repeated disaccharides of glucosamine, which is highly substituted with ester-linked long chain fatty acids (Westphal, 1975 and Luderitz et al. Int'l Sympo. on Pyrogen, Univ. College, London pp. 10–19, 1975). Furthermore, it was found that Lipid A is linked to core heteropolysaccharides by 2-keto-3-deoxyoctonic acid (KDO) which is unique to baterial liposaacharides but does not contribute to endotoxicity (Rietschel et al. 1973). It is the ester-linked fatty acids which are responsible for the biological activity. Removal of fatty acid residue abrogates the biological activity of Lipid A (Westphal, 1975, Bradley 1979, and Luderitz, 1975), but the remainder of the Lipid A molecule may determine solubility, conformation, distribution within the body and affinity for receptor site (Bradley 1979). Based on information described above, it may be concluded that human plasma contains an endotoxin-inactivator, which is most probably an esterase that detoxifies Lipid A by breaking off the ester-linked fatty acids.

The present invention for the isolation of an endotoxin-inactivator from human plasma involves three purification steps:

(1) Adsorption of plasma on DEAE-Sephadex followed by stepwise elution
(2) Adsorption of DEAE eluate on Cibacron-Blue sepharose (CBS) followed by stepwise elution, and
(3) Adsorption of the CBS elute on hydroxylapatite followed by stepwise elution The final product is homogeneous as judged by polyacrylamide gel eletrophoresis (PAGE), sodium-dodecyl sulfate PAGE (SDS-PAGE) and immunoelectrophoresis. The molecular weight of this protein is estimated as falling bewteen 61,000 and 65,000 as judged by SDS-PAGE and high performance liquid chromatography (HPLC).

The purified inactivator has been found to inactivate all three types of lipopolysaccharides tested; they are S. typhosa, S. enteritides and E. coli strain 055: 85. It has also been found that highly pyrogenic albumin can be made non-pyrogenic by mixing it with titrated amount of this inactivator. The inactivation of endotoxin was evidenced by the Limulus amebocyte lysate test in vitro and was further confirmed by the USP rabbit pyrogen test in vivo.

Chibata, U.S. Pat. No. 4,381,239 reveiws methods of removing pyrogen: (1) adsorption; (2) decomposition with acid or alkali; (3) decomposition with an oxidizing agent; or (4) filtration. Chibata taught that bacterial LPS is selectively adsorped by a heterocylic nitrogen compound.

The filtration of pyrogens from biological fluids is known. See Hou, U.S. Pat. No. 4,488,969; Grabner, U.S. Pat. No. 3,897,309; Chibata, U.S. Pat. No. 4,160,697; Nakamura, U.S. Pat. No. 4,259,448.

Mannuzza, U.S. Pat. No. 4,380,511 teaches the removal of pyrogens from blood protein products by absorbing the blood protein on blue dextran, washing away the pyrogen with a low ionic strength solution, and desorbing the column with a high ionic strength solution.

Babb, U.S. Pat. No. 4,381,004 speaks of a "microorganism deativator" for extracorporeal treatment of blood. However, this deactivator is an antimicrobial agent, not an inactivator of endotoxin. Babb provides for adsorption, rather than inactivation, of bacterial endotoxins.

Shanbrom, U.S. Pat. No. 4,069,216 discloses the "reworking" of pyrogenic lots of Factor VIII by a one or two step cold 6% PEG precipitation. The pyrogens are washed away from the Factor VIII precipitate. They are not inactivated. See also Shanbrom, U.S. Pat. No. 4,188,318.

Cano, U.S. Pat. No. 4,000,257 teaches use of ethyl or butyl acetate to extract endotoxins from an influenza virus vaccine to obtain a vaccine of low pyrogenicity.

Smith, U.S. Pat. No. 3,659,027 discloses destruction of pyrogens in water intended for parenteral use by strong alkali. Clearly, such harsh treatment is unsuitable for protein preparations.

Dasinger, U.S. Pat. No. 3,644,175 describes the inactivation (by acidification and heating) of endotoxins of gram-negative bacteria intended for use as a protein source.

Akcasu, U.S. Pat. No. 4,070,289 depyrogenates water by distillation under pressure.

GB No. 1,418,286 teaches the removal of pyrogens from urokinase (a product of human urine) by retaining the pyrogens on an anion exhange cellulose, such as diethylamino ethyl (DEAE) cellulose.

GB No. 1,557,545 teaches that urokinase can be reversibly absorbed on a hydrophilic polysaccharide which does not retain pyrogens.

DESCRIPTION OF THE PREFERRED EMBODIMENTS

In the method of the present invention for isolation of this endotoxin-inactivator (EI), it was carried out in a series of steps which are described hereinafter as Example 1.

The starting material can be fresh, fresh frozen, liquid, outdated plasma, cryo supernatant (after cryo precipitate is removed) or serum.

EXAMPLE 1

In essence, endotoxin-inactivator can be purified from plasma by three steps: namely, adsorption on DEAE-Sephadex and stepwise elution to remove the bulk of plasma proteins; adsorption on Cibacron-Blue-Sepharose and stepwise elution to remove the main contaminant, albumin; and adsorption on hydroxylapatite and stepwise elution to obtain a highly purified endotoxin-inactivator.

(1) DEAE-Sephadex Chromatography

Figure 1:
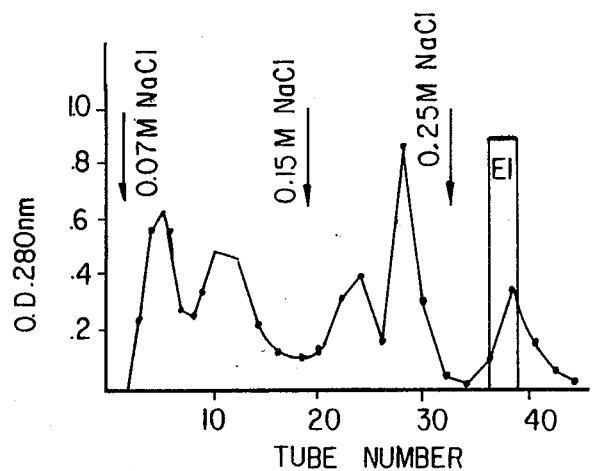
FIG. 1—Elution profile from DEAE-Sephadex chromatography (step 1).

FIG. 1 is the elution profile of protein distribution from DEAE-Sephadex. Dialyzed plasma, 50 ml, was applied to a column, 1.8×20 cm. Stepwise elution using 0.07M, 0.15M and 0.25M NaCl was then carried out. Each tube collected 15 ml eluate, and every second tube was assayed for activity. Buffer (0.02M Phosphate, pH 7.35) containing 0.07M NaCl eluted the residual reddish-colored fraction (transferrin) and a yellow-colored fraction, albumin. Buffer containing 0.25M NaCl eluted one protein peak with the inactivator activity concentrated in the ascending part of peak, and a slightly bluish fraction, which is ceruloplasmin, in the descending part of the protein peak. Fractions with inactivator activity were pooled according to their endotoxin inactivating activity as assayed by the LAL test system.

While DEAE-Sephadex Chromatography is preferred, those skilled in the art will recognize that other anion exchange chromatography techinques might prove fruitful. Elution at 0.25M NaCl is preferred, but salt concentrations ranging from 0.2-0.3M may prove useful.

(2) Cibacron-Blue Sepharose Chromatography

Figure 2:
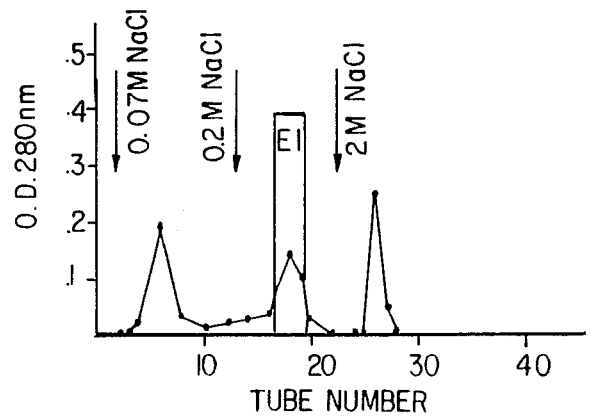
FIG. 2—Elution profile from Cibacron-Blue Sepharose chromatography (step 2).

FIG. 2 is the elution profile of protein distribution from Cibacron-Blue Sepharose. Diafiltered DEAE eluate containing EI was applied to the CBS column (1.25×20 cm) previously equilibrated with 0.02M phosphate buffer, pH 7.35. Stepwise elution using 0.07M, 0.2M and 2M McCl was then carried out. Each tube collected 10 ml eluate, and every second tube was assayed for activity. At 0.07M NaCl concentration, an inactive protein peak was eluted. At 0.20M NaCl concentration, a second protein peak with inactivator activity was eluted. At 2.0M NaCl concentration, a third protein peak, mostly albumin, was eluted. It should be noted that even though each of these peaks looked more or less symmetrical, it by no means represented only one protein.

It may be possible to substitute other dye affinity chromatographic separations for the preferred Cibracron-Blue Sepharose chromatographic step described herein. While elution at 0.2M NaCl is preferred, it is believed that a range of salt concentrations such as 0.15-0.25M will be efficacious.

(3) Hydroxylapatite Chromatography

Figure 3:
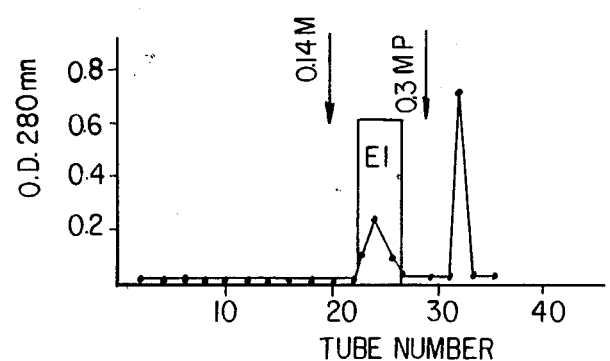
FIG. 3—Elution profile from hydroxylapatite chromatography (step 3).

FIG. 3 is the elution profile of protein distribution from hydroxylapatite chromatography. Diafiltered CBS eluate was applied to a HTP column (1×9.5 cm) previously equilibrated in 0.02M phosphate buffer pH 6.8. In order to obtain good flow rate 2 g of Sephadex G-25 was added to 10 g of HTP. Stepwise elution using 0.14M and 0.3M phosphate buffer, pH 6.8 was carried out. Tubes of 7 ml were collected. Fractions containing EI activity was eluted at 0.14M phosphate concentration at pH 6.8. Another protein peak was eluted at 0.3M phosphate concentration at the same pH.

It will be understood that those skilled in the art may be able to effect a further purification using another adsorption medium in place of hydroxylapatite. While elution at 0.14M phosphate is preferred, those skilled in the art may wish to employ concentrations of 0.1-0.25M phosphate.

(4) Yield, Recovery and EI Concentration

Based on the results of 5 runs each starting from 50 ml of fresh frozen plasma derived from 400 liter plasma pool an average yield of 1.4 mg of EI was obtained as assayed by Lowry (J. Biol. Chem. 193: 265, 1951). Since there was no report in the literature stating the concentration of EI in plasma, the percentage of recovery and concentration of EI are calculated as follows. Based on the activity assay, every 0.05 ml plasma inactivates 31.25 ng endotoxin standard (E. coli 055: B5). Therefore, 50 ml plasma would inactivate a total of 31,250 mg. It has also been found that every 0.05 ml EI preparation containing 0.014 mg EI would inactivate 2,560 ng which represents 8.2% recovery and the concentration of EI in plasma could therefore be calculated to contain $(31{,}250 \text{ ng}/2{,}560 \text{ ng}) \times 1.4 \text{ mg} = 17 \text{ mg}$ for every 50 ml or 34 mg/100 ml.

CHARACTERIZATION OF EI (1) Purity and molecular weight determinations

The purified EI was subjected to immunoelectrophoresis (IEP), polyacrylamide gel slab electrophoresis (PAGE), SDS-polyacrylamide gel slab electrophoresis (SDS-PAGE) and high performance liquid chromatography (HPLC).

Figure 4:
FIG. 4—Immunoelectropherogram of endotoxin inactivator.

FIG. 4 is the IEP result of the purified EI which shows one precipitation line when reacted with anti-whole serum. The conditions of the immunoelectrophoresis of EI were as follows: Top Well, EI, 7 µg; Bottom Well, Plasma (1:2), 5 µg; and Trough, anti whole serum 100 ul.

Figure 5:
FIG. 5—Polyacrylamide gel slab electropherogram of endotoxin inactivator.

FIG. 5 is the PAGE result of EI which shows one protein band (5A), midway between albumin and transferrin, when compared to that of plasma (5B). The conditions of the Polyacrylamide gel slab electrophoresis were as follows: Running gel 7.5% and stacking gel 3.5%; Endotoxin inactivator, 6 μg; and Plasma (1: 17), 5 μg.

Figure 6:
FIG. 6—SDS-PAGE analysis or endotoxin inactivator.

FIG. 6 is the result of SDS-PAGE, which again shows one protein band (6B) having a molecular weight of approximately 61,000 when calculated from the protein standards (6A). Protein standards (6A) are (from top down): myosin (H chain), 212,000; phosphorylase B, 97,500; bovine serum albumin, 68,000; ovalbumin, 43,000; alpha-chymotrypsinogen, 25,700 and beta-lactoglobulin, 18,400. EI (6B): 24 μg.

Figure 7:
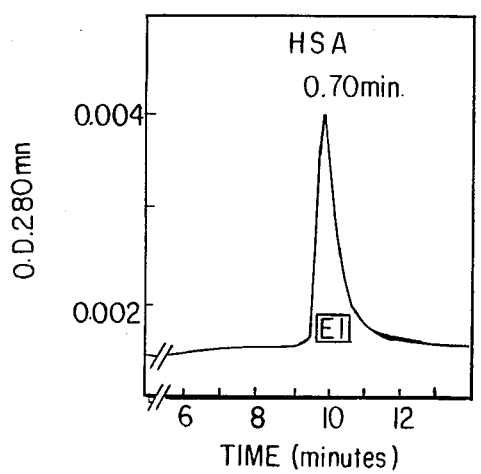
FIG. 7—HPLC elution profile of endotoxin inactivator mixed with pyrogenic albumin.

FIG. 7 is the HPLC result when EI is mixed with pyrogenic albumin. Based on these findings the molecular weight of EI is the same as albumin (HSA) which is 65,000. The test sample was made up from equal volume of human serum albumin (HSA), 0.15%, and EI, 0.12% in 0.05M phosphate, pH 7.0, containing 0.15M NaCl. The column used was TSK 3000, 7.5×300 mm.

(2) EI Activity

Lipopolysaccharide (LPS) derived from *Salmonella typhosa*, *Salmonella enteritides* and *Escherichia coli* 0.55:B5 of 2-fold serial dilutions were mixed with EI and the endotoxins remained in the mixture were assayed by LAL with the sensitivity of the lysate being 0.05 ng/ml. The LAL assay is based on the discovery by Bang, John Hopkins Hosp., 98: 325 (1956) of the gelation of a lysate of amebocyte of Limulus, the horeshoe crab. The results are shown in Table 1. The last column of the table is the total nanogram of LPS inactivated per mg of EI calculated from the results in the reaction mixture (middle column).

TABLE 1

INACTIVATION OF VARIOUS LPS BY ENDOTOXIN INACTIVATOR

| LPS | NG INACTIVATED IN 0.5 ML 0.014 MG EI | NG INACTIVATED MG EI |
| --- | --- | --- |
| S. Typhosa | 51.2–102.4 ng | 3,657–7,314 ng |
| S. enteritides | 12.8–25.6 ng | 914–1,829 ng |
| E. coli 055:B5 | 12.8–25.6 ng | 914–1,829 ng |

Because of the nature of the LAL assay in which LPS solutions were prepared by 2-fold serial dilutions, the EI activity toward each LPS was expressed in a range for the given amount of EI. Although it has been known that LPS derived from one type of bacteria could be as much as 6 times more potent than the other (Greisman and Hormick, Proc. Soc. Exp. Biol. Med. 131: 1154, 1969), the purity of each LPS used in these experiments were not necessarily the same thus resulting, at least in part, in the different ranges of inactivation.

(3) Rabbit Pyrogen Test

In order to ascertain that the inactivation was not a result of inhibition of the LAL test but as a result of the detoxification of the endotoxins, an aliquot of a highly pyrogenic 25% albumin solution having an endotoxin level of 12.8 ng/ml was divided into two vials, 25 ml each. To one vial, 0.125 mg of EI in 0.89 ml of 0.02M phosphate, pH 7.35, was added, and to the second vial (Control) 0.89 ml of plain buffer was added. Both vials were then incubated at 37 deg. C. for 15 min. and rabbit pyrogen tests (3 ml/kg) were carried out. The results showed that the Control, which was not treated with EI, induced an aggragate temperature rise of 2.1 deg. C. (0.2, 0.9, 1.2 deg. C.) whereas the EI-treated albumin induced an aggregate temperature rise of 0.4 deg. C. (0.0, 0.0, 0.4 deg. C.), clearly suggesting that the endotoxin had been detoxified. (Any parenteral intended for clinical use has to pass the rabbit pyrogen test with an induced temperature rise not greater than a total of 1.5 deg. C. for three rabbits, and none of the three rabbits may have a temperature rise of more than 0.5 deg. C.). The term "essentially nonpyrogenic", as used herein, means a preparation which passes the USP rabbit pyrogen test.

The term "endotoxin inactivator" encompasses substances which merely reduce the pyrogenic activity of an endotoxin sufficiently to render an endotoxin containing composition "essentially nonpyrogenic."

(4) Stability of EI

Preliminary results indicate that the activity of EI prepared by this procedure appears to be stable for up to 48 hours at +5 C. Whereas, samples kept at −20 C. and −80 C. remained active even after one month.

Products such as AHF and Factor IX complex are routinely isolated prior to ethanol fractionation. If there is a need of EI, it appears feasible to incorporate the present procedure into the scheme when Factor IX complex is isolated, since the procedure also involves the use of DEAE-Sephadex. (Heystek, et al., Vox Sang, 25: 113, 1973.) After DEAE-Sephadex adsorption and prior to elution of Factor IX complex at 2.0M NaCl, a wash step using 0.15M NaCl elutes most of the albumin which is to be added to the starting plasma for recovery of albumin. An additional stepwise elution of the DEAE-cake at 0.25M NaCl would yield a partially purified EI which could be further purified without interfering with the recovery of either albumin or Factor IX complex.

As described above, the first step of the purification procedure was to adsorb dialyzed plasma on DEAE-Sephadex followed by stepwise elution at different ionic strength. Partially purified EI was eluted at 0.25M NaCl in 0.02M phosphate buffer, pH 7.35. This step, with modification, could conceivably be incorporated into the procedure for isolation of Factor IX complex. One of the widely used procedures, Suomela, et al., Vox Sang, 33:37 (1977), for isolation of Factor IX complex (II, VII, IX and X) consists of adding DEAE-Sephadex (1.5 g/L plasma) to plasma or cryo supernatant, washing DEAE cake with 0.01M sodium citrate buffer containing 0.15–0.17M NaCl, pH 7.0 and eluting Factor IX complex with 0.03M sodium citrate containing 2M NaCl. The present method for isolation of EI requiring 0.25M NaCl in 0.02M phosphate buffer could be readily incorporated inbetween the washing and eluting steps. It is expected that the introduction of an additional elution step for EI would result in an insignificant reduction in the overall yield of Factor IX due to partial elution of Factor VII at this ionic strength, but the specific activity of the final products in terms of Factor IX should be higher since Factor IX remains tightly bound under such conditions.

It will be apparent that various changes may be made in the method as described herein without departing from the spirit and scope of the invention or sacrificing its material advantages, the forms hereinbefore described being merely preferred embodiments thereof.

REFERENCES

Bradley, S.G. Ann. Rev. Microbiol. 33:67–94, (1979).
Cohn, et al. JACS 68:459–475, (1946).
Galanos, et al. Eur. J. Biochem, 31:230–233, (1972).

Greisman, Proc. Soc. Exp. Biol. Med. 131:1154 (1969).
Hao, Vox Sang 36:313–320, (1079).
Hao. Y.L. Depryogenation of Clinical albumin, U.S. Patent pending serial number 06/635, 134, filed July 27, 1984.
Hegemann, F. A. Immunitactsforsch. 111:213–225, (1954).
Johnson, et al. Am. J. Pathol. 88:559–574, (1977).
Landy, et al. J. Exp. Med. 110:731–750, (1959).
Levin, et al. J. Lab. Clin. Med. 75:903 (1970).
Lowry, et al. J. Biol. Chem. 193:265 (1951).
Luderitz, et al. Int'l symposium on Pyrogen, University College, London p. 10–19, (1975).
Univ. of Chicago Press, pp. 9–21, (1973).
Rall, et al. Am. J. Physiol. 188:559–562, (1957).
Rietschel, et al. Eur. J. Biochem, 22:218–224, (1971).
Rietschel, et al. Immunity 8:173–177, (1973).
Rudbach, et al. J. Immunol. 89:326–335 (962).
Schneider, et al. Blut 30:121–134, (1975).
Skarnes, Ann. N.Y. Acad. Sci. 133:644–662, (1966).
Skarnes, et al. J. Exp. Med 108:685–700, (1958).
Westphal, Int. Archs. Allergy Appl. Immun. 49:1–43, (1975).
Wye, et al. Vox Sang 32:182–184, (1977).
Yoskioka, et al. J. Immunol. 89:326–335. (1962).

I claim:

1. A method of depyrogenating a pyrogenic blood product which comprises providing a pyrogenic blood product, and adding an endotoxin inactivating amount of endotoxin inactivator derived from blood and characterized as follows:
   (a) a molecular weight of about 61,000 daltons;
   (b) elution of about 0.2–0.3M NaCl form a DEAE-Sephadex adsorbent;
   (c) elution at about 01.5–0.25M NaCl from a Cibacron-Blue-Sepharose adsorbent; and
   (d) elution at about 0.1–0.25M phosphate from a hydroxyapatite adsorbent.

2. The method of claim 1 wherein the endotoxin inactivator is provided in essentially pure form.

3. The method of claim 2, wherein the inactivator is capable of inactivating at least about:
   3,657 ng *S. typhosa* endotoxin,
   914 ng *S. enteritides* endotoxin, or
   974 ng *E. coli* 055:B5 endotoxin, per milligram of endotoxin inactivator.

4. The method of claim 2, wherein the endotoxin inactivator is provided in essentially pure form by subjecting an endotoxin-inactivator-containing fraction of blood to DEAE-sephadex chromatography, immobilized chromophore blue chromatography, and hydroxyapatite chromatography.

5. The method of claim 2 in which the endotoxin inactivator is essentially stable.

6. An essentially nonpyrogenic blood product suitable for parenteral administration consisting essentially of a first blood protein and an essentially stable endotoxin inactivator derived from blood.

7. The product of claim 6 in which the first blood protein is an immunoglobulin.

8. The product of claim 6 in which the first blood protein is antihemophilic factor.

9. The product of claim 6 in which the first blood protein is Factor IX.

10. The product of claim 6 in which the first blood protein is an interferon.

11. A method for the purification of Factor IX complex and endotoxin inactivator from which comprises:
    (a) subjecting the plasma to DEAE-Sephadex chromatography;
    (b) eluting the endotoxin inactivator in partially purified from with an eluting buffer containing about 0.2–0.3M NaCl;
    (c) eluting the Factor IX complex with an eluting buffer containing about 2M NaCl;
    (d) subjecting the partially purified endotoxin inactivator of step (b) to Cibacron-blue Sepharose chromatography to yield a further purified endotoxin inactivator; and
    (e) subjecting the further purified endotoxin inactivator of step (d) to hydroxyapatite chromatography to yield endotoxin inactivator in essentially pure form.

* * * * *